United States Patent [19]
Barbara

[11] 4,141,344
[45] Feb. 27, 1979

[54] SOUND RECORDING SYSTEM

[76] Inventor: Louis J. Barbara, 7027 SW. 87 Ct., Miami, Fla. 33173

[21] Appl. No.: 882,777

[22] Filed: Mar. 2, 1978

[51] Int. Cl.² ............................................. A61M 21/00
[52] U.S. Cl. .................................................. 128/1 C
[58] Field of Search ................... 128/1 C, 1 R, 2.1 B; 328/158, 160; 360/18

[56] References Cited
U.S. PATENT DOCUMENTS

| | | | |
|---|---|---|---|
| 3,400,333 | 9/1968 | Inose | 328/160 |
| 3,576,185 | 4/1971 | Schulz et al. | 128/1 C |
| 3,712,292 | 1/1973 | Zentmeyer, Jr. | 128/1 C |

Primary Examiner—William E. Kamm
Attorney, Agent, or Firm—Oltman and Flynn

[57] ABSTRACT

In recording an audio program, such as music or voice, on a magnetic tape recorder an A.C. signal generator operating at a frequency below about 14 Hz. provides an A.C. baseline for the audio program signal. This 14 Hz. or lower A.C. signal is sensed by the listener's ear to create an Alpha or Theta state in his brain when the tape is played back.

9 Claims, 3 Drawing Figures

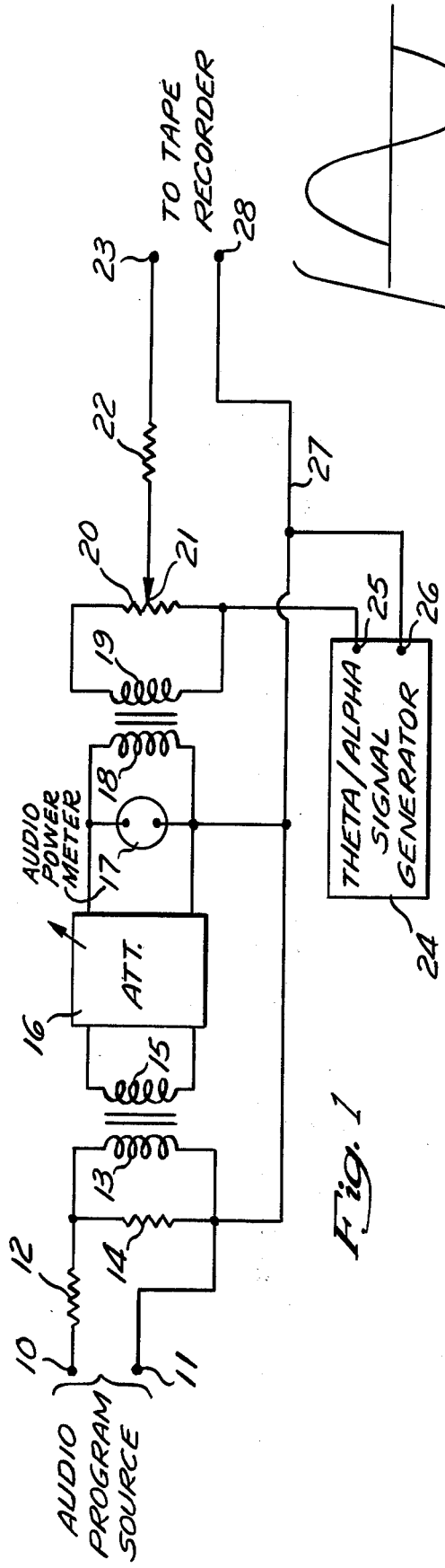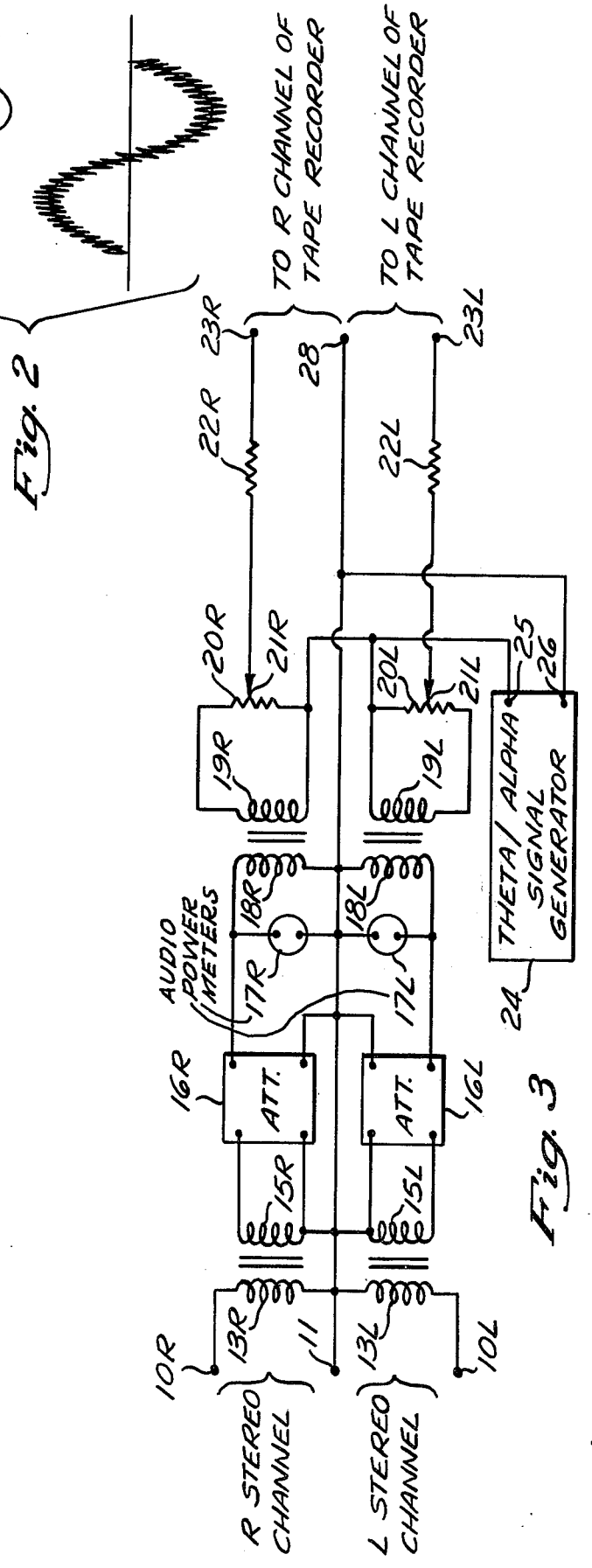

SOUND RECORDING SYSTEM

BACKGROUND OF THE INVENTION

Various methods have been used heretofore to put the human brain into a Theta (below 7 Hz.) or Alpha (7-14 Hz.) brain wave state.

The Alpha state of the brain is considered desirable as promoting relaxation of the body, reducing or eliminating anxiety or mental stress, enhancing the brain's efficiency and creativity, and promoting a feeling of peace and silence.

The Theta state of the brain is associated with peaceful sleep.

In considering the possibility of using conventional magnetic tape recordings to induce the Theta or Alpha state, the first, seemingly insuperable problem is the low frequency limit of conventional tape recording/playback instruments. Those in the low price range (e.g., below $60) typically are not designed for frequencies below 200 Hz. Those in an intermediate price range (e.g., $95-175) typically can handle frequencies down to about 70 Hz. Even tape recorders/players in the price range above $1,000 cannot adequately record or reproduce signal frequencies below 20 Hz.

SUMMARY OF THE INVENTION

The present invention is directed to a novel apparatus and method which enables relatively inexpensive magnetic tape players to be used to stimulate Theta or Alpha brain wave patterns in the listener.

In accordance with the present invention, an audio program is recorded on tape, consisting of signals completely or virtually completely within an audio frequency range substantially above 14 Hz. This audio program may be music, voice, white noise, single frequency tones, or combinations of several different single frequency tones. During the recording of this audio program, which in and of itself would present no difficulty to the recording apparatus, the baseline of the audio program is varied in accordance with a Theta or Alpha signal, which preferably is a single frequency signal, such as 10.53 Hz. Alpha signal. The Theta or Alpha signal provides a very low frequency A.C. baseline for the audio program signal in place of the usual baseline at ground potential. Preferably, the amplitude of the Theta or Alpha baseline signal is about four times the maximum amplitude of the audio program signal, such as music or voice.

It has been found that magnetic tape recordings made this way, when played back, are effective in inducing a beneficial Theta or Alpha state in the listener's brain even though the listener may be only conscious of hearing the music, voice or other audio program from the tape. Also, some listeners with hearing problems are better able to hear the music, voice or other audio program recorded this way.

Two presently preferred apparatus embodiments of this invention are illustrated in the accompanying drawings in which:

FIG. 1 is a schematic electrical circuit diagram of a monaural recording arrangement in accordance with the present invention;

FIG. 2 shows the wave form of the output signal from the Theta/Alpha signal generator in FIG. 1 and below it the wave form of the input signal to the tape recorder; and FIG. 3 is a schematic electrical circuit diagram of a stereophonic (binaural) recording arrangement in accordance with this invention.

Before explaining the disclosed embodiments of the present invention in detail, it is to be understood that the invention is not limited in its application to the details of the particular arrangements shown since the invention is capable of other embodiments. Also, the terminology used herein is for the purpose of description and not of limitation.

Referring first to FIG. 1, the input terminals 10 and 11 of the present apparatus receive an audio program from a suitable source of music, speech, white noise, etc., which produces signals which are entirely or very predominantly within the audio frequency range substantially above 14 Hz. For purposes of this discussion, this audio program will be referred to hereinafter as music.

The upper audio program input terminal 10 is connected through a resistor 12 to the upper end of the primary 13 of a first stepdown transformer. The lower audio program input terminal 11 is connected directly to the lower end of the transformer primary 13. A shunt resistor 14 is connected across the transformer primary 13.

This transformer has a secondary winding 15 connected through an attenuator or adjustable volume control 16 and an audio power meter 17, both of known design, across the primary 18 of a step up transformer. This transformer has a secondary winding 19 connected across a potentiometer resistance 20. An adjustable tap 21 on the potentiometer is connected through a resistor 22 to a first input terminal 23 leading to the tape recorder.

A signal generator 24, which produces a sine wave falling somewhere within the Theta/Alpha frequency range below 14 Hz., has a first output terminal 25 connected to the lower end of the potentiometer 20 and the transformer secondary 19. This signal generator has a second output terminal 26 which is connected via line 27 to the remaining input terminal 28 for the tape recorder. Line 27 also is connected to the music program input terminal 11 and the lower end of the primary 18 of the second transformer. Line 27 may be grounded to the chasis of the signal generator 24 on the meter 17. Preferably, both the frequency and the amplitude of the output signal from the generator 24 are selectively adjustable.

In one practical embodiment of this circuit the ohmic value of each resistor 12, 14, 20 and 22, the first transformer primary 13 and the second transformer secondary 19 is 10,000 ohms, and the ohmic value of the first transformer secondary 15 and of the second transformer primary 18 is 500 ohms. In this embodiment, each transformer is designed for a frequency response of from 20 to 20,000 HZ. and has a power rating of 10 watts, and the generator 24 produces a 10.53 Hz. sine wave.

In the use of this recording arrangement, with the signal generator 24 disconnected or de-energized the attenuator 16 is adjusted to provide a zero decibel reading on the audio power meter 17. A cathode ray oscilloscope (not shown) is connected across the input terminals 23 and 28 for the tape recorder. With the time base of the oscilloscope adjusted to 1 millisecond, the adjustable potentiometer tap 21 is adjusted to provide a maximum input signal of 0.2 volt peak-to-peak on the oscilloscope. Then the oscilloscope time base is set for 10 milliseconds and its trigger level is set for one complete wave form. The Theta/Alpha signal generator 24 is energized at the desired frequency within the range below 14 Hz. and the amplitude of its output signal across terminals 25 and 26 is adjusted to read 0.8 volt peak-to-peak on the oscilloscope. Thus, with this adjustment the Theta/Alpha signal has an amplitude four times the mean amplitude of the music or other audio program signal and substantially greater than the maximum amplitude of the audio program signal.

After these adjustments have been made, this circuit provides the proper input to the terminals 23 and 28 for the tape recorder. Preferably, these terminals are connected through a shielded input cable to the tape recorder.

The upper curve in FIG. 2 shows the sinusoidal Theta or Alpha signal appearing across the output terminals 25 and 26 of the signal generator 24.

The lower curve in FIG. 2 shows the signal which is applied across the input terminals 23 and 28 for the tape recorder. This signal is made up of the music signals added to the Theta or Alpha signal appearing across the signal generator output terminals 25 and 26. In effect, this latter signal provides a sinusoidally fluctuating base line (at the Theta or Alpha signal amplitude and frequency) for the music signal, so that the instantaneous amplitude of the music signal with respect to ground is the sum of the amplitudes of both the music signal input per se and the much lower frequency Theta or Alpha signal from generator 24.

While the ratio of the amplitude of the Theta/Alpha component to the mean amplitude of the music, voice or other audio program component of the composite input signal appearing across terminals 23 and 28 preferably is 4 to 1, this ratio may be as low as 3 to 1, or as high as 5 to 1 with satisfactory results. If this ratio is less than about 3 to 1, the Theta or Alpha signal component is not strong enough to reliably be sensed by the listener's ears when the tape is played back. On the other hand, if this ratio is above about 5 to 1 the audio program, such as music or voice, is of such low amplitude as to be unsatisfactory to a typical listener when the tape is played back.

I have found that, when the tape is played back by the usual tape recorder and the played-back signal is displayed on an oscilloscope, the mean amplitude of the music, voice or other audio program is much larger than the Theta or Alpha component. However, the latter component is present with a large enough amplitude to induce a Theta or Alpha state in the listener's brain. This happens even though neither the magnetic recording tape nor the playback equipment is designed to effectively handle signal frequencies of 14 Hz. or lower.

The Alpha state may produce in the listener a sensation of lightly varying pressures within the body, a tingling sensation at the skin, a flicking of the eyelids, or a feeling of warmth in some parts of the body. Some listeners with hearing problems report an enhanced ability to hear both music and voice. A noticeable enhancement of the vibrato of a singer's voice is obtained when Alpha tones are recorded along with the voice, and in playback the listener naturally attributes this improved vibrato to the singer's voice and not to any observable recording technique.

FIG. 3 shows a second embodiment of the present invention which provides a stereo tape recording. For convenience the two stereo channels may be referred to as "left" and "right" and the circuit elements are designated "L" or "R" according to the channel to which they belong. Circuit elements in the individual "left" or "right" channel which correspond in function to those in the monaural circuit of FIG. 1 are given the same reference numerals as in FIG. 1 but with an "L" or "R" suffix added.

In FIG. 3 a single Theta/Alpha signal generator 24 is provided for both the right and left channels of the music or other audio program input. The input signal to the tape recorder which appears across terminals 23R and 28 consists of the Theta or Alpha baseline signal component with the right channel of the music or other audio program superimposed upon it in additive fashion. The input signal to the tape recorder which appears across terminals 23L and 28 consists of the same Theta or Alpha baseline signal component and the left channel of the music or other audio program added to it.

The individual channels of the FIG. 3 recording arrangement operate substantially as already described with reference to FIG. 1, and this detailed description need not be repeated.

Various modifications of the disclosed embodiments of the invention are possible. For example, the output of the Theta/Alpha signal generator may be a triangular wave instead of a sine wave, if desired. Also, various changes may be made in the circuitry for combining the Theta/Alpha signal with the music or other audio program signal.

I claim:

1. In a recording system for a sound recorder having an input, the combination of:
    a signal generator for generating an A.C. signal of predetermined amplitude within the frequency range below about 14 Hz.;
    means for combining additively with said A.C. signal an audio program signal falling substantially within a frequency range substantially above 14 Hz. and of substantially smaller amplitude than the maximum amplitude of said A.C. signal;
    and means for applying the additively combined audio program signal and A.C. signal to the sound recorder input.

2. A recording system according to claim 1, wherein said A.C. signal has an amplitude within the range from about three to five times the mean amplitude of said audio program signal.

3. A recording system according to claim 1, wherein said A.C. signal is a sine wave with an amplitude substantially four times the mean amplitude of said audio program signal.

4. A recording system according to claim 1, wherein said means for combining the audio program signal with said A.C. signal comprises:
    step-down transformer means having a primary and a secondary;
    means for applying the audio program signal to the primary of said step-down transformer means;
    volume control means having its input operatively connected to the secondary of said step-down transformer means;
    step-up transformer means having a primary operatively connected to the output of said volume control means and having a secondary;
    potentiometer means operatively connected to the secondary of said step-up transformer means, said potentiometer means having an adjustable tap connected to one input terminal of said sound recorder;

and means connecting said A.C. signal generator across one terminal of said potentiometer means and another input terminal of the sound recorder to add said A.C. signal to said audio program signal.

5. A recording system according to claim 4, wherein:
said primary of said step-up transformer means has one terminal thereof connected directly to said other input terminal of the sound recorder;
and said primary of said step-down transformer means has one terminal thereof connected directly to said other input terminal of the sound recorder.

6. A recording system according to claim 5, wherein:
said step-up transformer means is a single transformer;
said step-down transformer means is a single transformer;
and the input to the sound recorder has just two input terminals.

7. A recording system according to claim 5, wherein:
said step down transformer means consists of two transformers, one for each stereo channel;
said volume control means consists of two separate volume controls operatively connected respectively to the individual step-down transformers;
said step-up transformer means consists of two separate transformers operatively connected respectively to the individual volume controls;
and the input to the sound recorder has three input terminals, one of which is said other input terminal to which that A.C. signal generator is connected.

8. A recording system according to claim 4, wherein said A.C. signal has an amplitude within the range from substantially three to five times the mean amplitude of said audio program signal.

9. A recording system according to claim 5, wherein said A.C. signal is a sine wave with an amplitude substantially four times the mean amplitude of said audio program signal.

* * * * *